United States Patent [19]

Benin et al.

[11] Patent Number: 4,501,951
[45] Date of Patent: Feb. 26, 1985

[54] ELECTRIC HEATING ELEMENT FOR STERILELY CUTTING AND WELDING TOGETHER THERMOPLASTIC TUBES

[75] Inventors: Joshua Benin; Robert P. Luoma, II, both of Newark, Del.

[73] Assignee: E. I. Du Pont de Nemours and Company, Wilmington, Del.

[21] Appl. No.: 408,417

[22] Filed: Aug. 16, 1982

[51] Int. Cl.³ ............... B29C 27/06; H05B 3/10; B26D 7/10

[52] U.S. Cl. .................. 219/243; 30/140; 83/171; 156/251; 156/304.6; 156/515; 156/518; 156/583.1; 219/221; 219/227; 219/544; 338/248; 338/250; 338/251; 338/255; 604/408

[58] Field of Search ........... 219/221, 230, 227, 229, 219/544, 534; 156/304.2, 304.6, 503, 515, 518, 579, 583.1, 583.2, 251; 30/140; 83/170, 171; 604/408; 338/243–251, 254–257

[56] References Cited

U.S. PATENT DOCUMENTS

| | | | |
|---|---|---|---|
| 1,005,360 | 10/1911 | Taylor | 338/251 |
| 1,705,696 | 3/1929 | Woodson | 338/248 X |
| 2,425,088 | 8/1947 | Dean | 338/254 X |
| 2,615,111 | 10/1952 | Paquette et al. | 83/170 |
| 2,859,321 | 11/1958 | Garaway | |
| 2,863,036 | 12/1958 | Mitchell et al. | 30/140 |
| 2,866,068 | 12/1958 | Bernstein | 30/140 X |
| 3,010,007 | 11/1961 | Theodore et al. | 219/544 X |
| 3,922,386 | 11/1975 | Ros | |
| 4,369,779 | 1/1983 | Spencer | 604/408 |

FOREIGN PATENT DOCUMENTS 596140  7/1959  Italy .................... 156/251

OTHER PUBLICATIONS

"Thermofoil Heat Fusers", Bulletin TF-5, Revised Mar. 1975, Minco Products, Inc., Minneapolis, Minnesota.

"Thermofoil Heaters", Bulletin TF-4, revised Aug. 1973, Minco Products, Inc., Minneapolis, Minnesota.

Primary Examiner—A. Bartis

[57] ABSTRACT

An electric heating element for sterilely cutting and welding together a pair of thermoplastic tubes transversely of the axis of each tube includes as an outer layer a folded sheet of a metal, such as copper, aluminum, silver or gold, having a thermal conductivity of at least about 173 watts/m°K at a thickness of 0.10 mm and a tensile yield strength of at least $34 \times 10^4$ kPa at a 0.10 mm thickness. A resistance heating element, preferably having a positive thermal coefficient of resistance (PTC), in the form of a resistor of stainless steel or the like is disposed inside the fold of the metal sheet and a layer of dielectric adhesive, such as an epoxy or acrylic adhesive, stable to about 260° C., is disposed between the inner surfaces of the metal sheet and the resistor to insulate the resistor from the folded sheet and bond the resulting structure together. The folded edge of the metal sheet forms the melting edge of the heating element. The heating element has a thickness of from about 0.13 mm. to about 0.76 mm.

22 Claims, 3 Drawing Figures

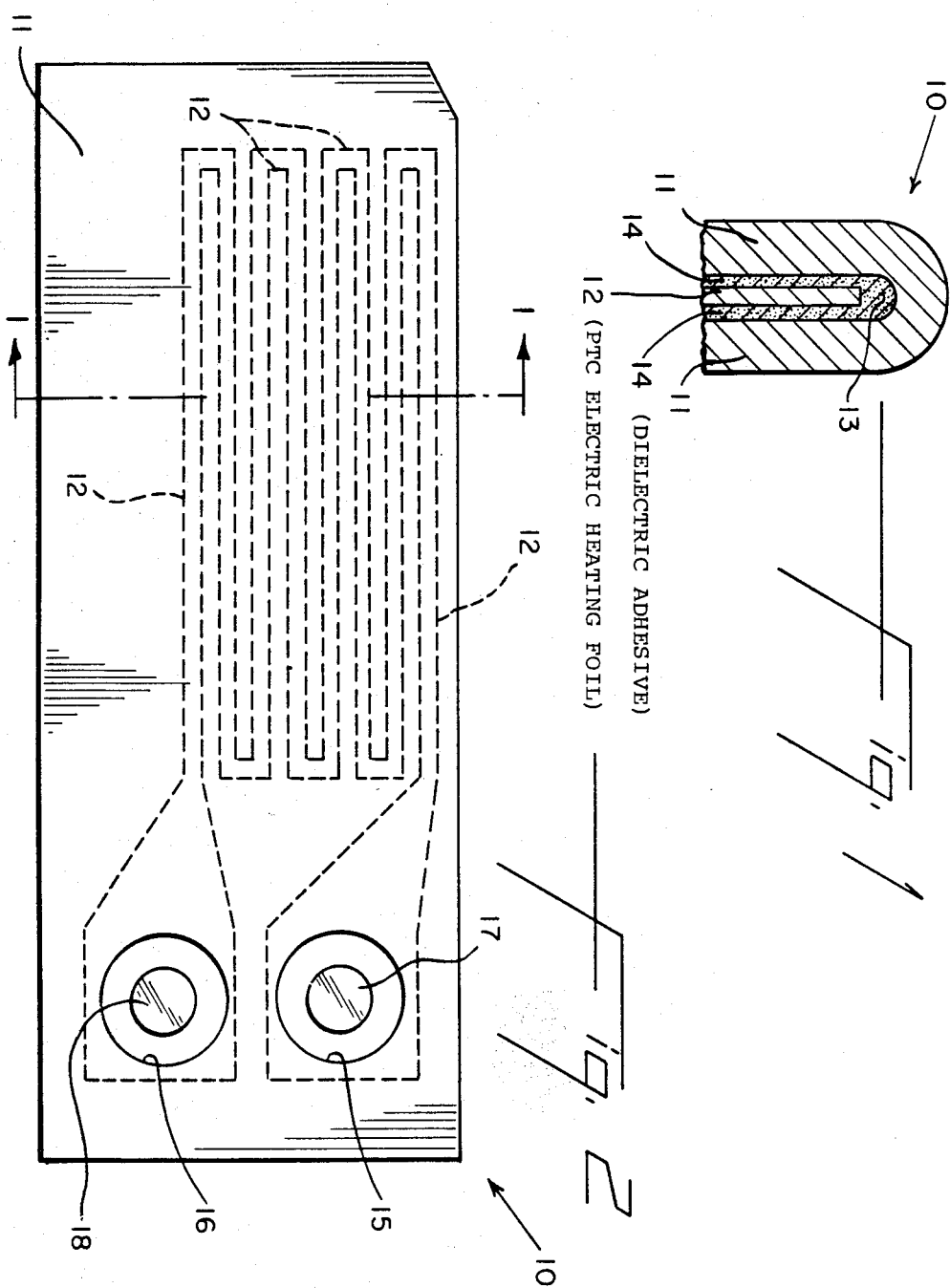

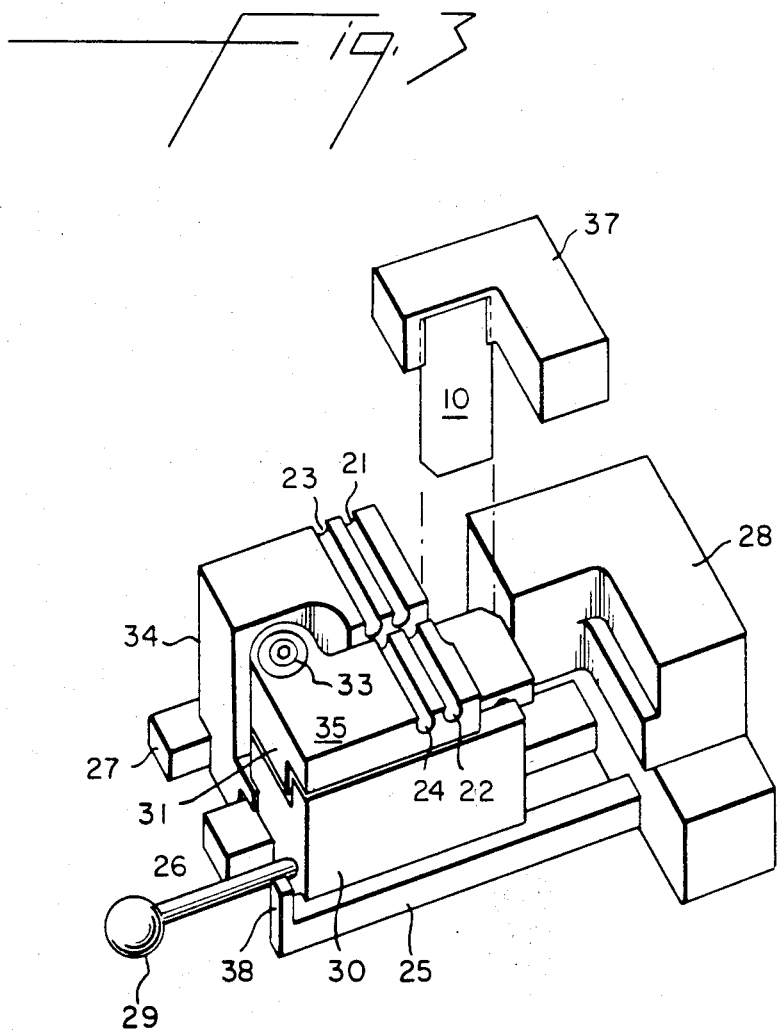

4,501,951

ELECTRIC HEATING ELEMENT FOR STERILELY CUTTING AND WELDING TOGETHER THERMOPLASTIC TUBES

BACKGROUND OF THE INVENTION

This invention relates to a printed circuit heating element. More specifically the present invention relates to a printed circuit heating element suitable for heating and welding two thermoplastic tubes together.

U.S. patent application Ser. No. 267,291 filed on June 4, 1981, now U.S. Pat. No. 4,369,779, discloses an apparatus for forming a sterile connection comprising a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together. The application discloses that the cutting means can take many forms but preferably is a laminate strip constructed of an etched stainless steel ribbon having on each side an acrylic adhesive layer, an aromatic polyimide layer, an acrylic adhesive layer and a copper ribbon.

During the use of the sterile docking apparatus of the aforesaid patent, it has been found that printed circuit cutting means made of the aforesaid laminate suffered breakdown of the adhesive in the inner adhesive layer and displayed insufficient mechanical strength, thereby resulting frequently in unsatisfactory welds, e.g., lack of strength. There exists a need for advantageous solutions to the problems of adhesive breakdown, insufficient mechanical strength and poor dissemination of heat to the outside of the cutting means.

Printed circuit heating elements are well known. Many of these elements involve either a metal substrate having a ceramic coating with a resistor layer adhered to the coating or an etched resistor laminated with layers of adhesive to insulation, which is often an aromatic polyimide resin, which is laminated with additional layers of adhesive to a metal cover.

U.S. Pat. No. 2,859,321, issued to Garaway on July 11, 1955, discloses an electrical resistance heating device in which printed heating elements are applied to one side of a metal base, the heating elements being insulated from the base by means of a devitrified ceramic enamel coating applied therebetween.

U.S. Pat. No. 3,922,386, issued to Ros on Nov. 25, 1975, discloses a heating element for use with printed circuits and which is itself a printed circuit comprising a filament consisting of a mixture of aluminum and aluminum oxide, the resistivity of the heating element formed of the filament being adjustable by varying the thickness of the filament. The filament is supported on a ceramic coating on a metal substrate.

SUMMARY OF THE INVENTION

The present invention provides a heating element for welding first and second thermoplastic tubes together transversely of the axis of each tube comprising, as an outside layer, a folded sheet of a metal having a thermal conductivity of at least about 100 BTU ft/hr. ft$^2$ °F. and a tensile yield strength of at least about $34 \times 10^4$ kPa (5000) psi, both at 0.10 mm thickness; a resistor disposed inside the fold of said sheet of metal; and a layer of dielectric adhesive, stable to about 260° C., between inner surfaces of said folded sheet of metal and surfaces of said resistor, thereby bonding the resulting structure together.

BRIEF DESCRIPTION OF THE DRAWING

FIG. 1 is a fragmentary sectional view of a heating element in accordance with the present invention taken along 1—1 of FIG. 2.

FIG. 2 is a plan view of a heating element in accordance with the present invention.

FIG. 3 is a perspective view of a sterile connection apparatus containing the heating element of FIG. 2.

DETAILED DESCRIPTION OF THE INVENTION

Referring now to FIG. 1, heating element 10 has a folded sheet 11 of metal, which in the figure is copper, as an outer layer. Disposed within the fold 13 of the sheet 11 is resistor 12 which is made from etched stainless steel foil for this embodiment. Also, disposed within fold 13 adjacent to the inner surfaces of sheet 11 and surrounding the resistor on both sides and one edge is dielectric adhesive layer 14 which in the figure is acrylic adhesive. The folded edge of the outer layer of the heating element serves as the cutting surface.

Referring now to FIG. 2, heating element 10 is shown with resistor 12. Openings 15 and 16 are provided on one side of folded sheet 11 thereby exposing terminals 17 and 18 of resistor 12.

Folded sheet 11 can be a single sheet or can be comprised of 2 or 3 sheets functioning as a single sheet. For instance, when two sheets are used, one may be folded with a J-shape and the other forms the other side by being mechanically crimped to the J-shaped sheet. When three sheets are used, one sheet would form the curve or fold and the other two could be mechanically crimped thereto to form the sides. Other modes of having the sheets cooperate together as one will be readily apparent to the practitioner. Folded sheet 11 is made from a metal having a terminal conductivity of at least about 173 watts/m °K. (100 BTU ft/hr ft$^2$ °F.) for a 0.10 mm (4 mil) thickness and a tensile yield strength of at least about $34 \times 10^4$ kPa (5000 psi) for a 0.10 mm (4 mil) thickness. Good thermal conductivity is required primarily to distribute heat evenly along the metal surface thereby avoiding hot spots. It is known that heat flow due to conductance is proportional to thermal conductivity, area perpendicular to heat flow, and thermal gradient. Therefore, a thicker sheet, with higher cross-sectional area, could provide the same heat flow (for a given gradient) with a metal of lower thermal conductivity. Thus, if sheet 11 is thicker than 0.10 mm, a thermal conductivity proportionately less than 173 watts/m °K. is suitable. A high thermal conductivity as required herein also imparts to the heating element capability to maintain a satisfactory surface temperature during use, i.e., when melting through two tubes to be joined.

The metal of the outer layer must have adequate strength to withstand the working load to which the heating element is subjected. A tensile yield strength of at least $34 \times 10^4$ kPa (5000 psi) at 0.10 mm thickness is adequate for this purpose. A thicker sheet, with higher crosssectional area, could resist the same working load with a metal of lower strength. Thus, if sheet 11 is thicker than 0.10 mm, a tensile yield strength proportionately less than $34 \times 10^4$ kPa would also be suitable to resist the working load during use. The metal also has to be sufficiently malleable so that the sheet can be folded without cracking or splitting. The metal must be compatible with any fluid contained in bags to which the tubing being cut is connected, i.e., the metal should not, at the temperature of use, react to give off products deleterious to the recipient of the fluid contained in the bag.

Metals suitable for use in making the folded sheet 11 include copper, aluminum, silver, gold and alloys of any of these metals. Preferably, the metal is copper, particularly rolled, annealed copper.

Resistor 12 can have a positive, negative or zero thermal coefficient of resistance, however, a positive thermal coefficient of resistance (ptc) is preferred. The resistor can be made from a serpentine piece of wire, a stamped foil, or an etched foil. Preferably, the resistor is an etched foil resistor made from stainless steel or from Nichrome having 15% chromium by weight. Most preferably, the resistor is an etched foil resistor made from stainless steel, particularly type 302 stainless steel.

A dielectric adhesive is used to bond the outer layer and the resistor together. In addition to serving as a bonding agent, the adhesive prevents the occurrence of electrical continuity between the resistor and the outer layer of the heating element. The adhesive should have a dielectric strength sufficient to insulate against a 24 VDC (volts direct current) potential at about 260° C. (500° F.) in the thin layer used in the heating element of the invention. The adhesive should also display adequate peel strength at about 260° C. to resist delamination of the heating element. A peel strength of at least about 1 lb/inch at 20° C. is typically sufficient for this purpose. The dielectric adhesive should be relatively resistant to melting and electrical breakdown at temperatures of about 260°-316° C. (500°-600° F.) for about 15-20 seconds. Suitable adhesives include acrylic adhesive, epoxies, and RTV (room temperature vulcanizing) silicones but epoxy and acrylic adhesives are preferred with an acrylic adhesive being most preferred. "Pyralux" acrylic adhesives made by E. I. du Pont de Nemours and Company have been found to be satisfactory.

Heating element 10 can have a thickness of from about 0.13 mm (5 mil) to about 0.76 mm (30 mil), preferably from about 0.25 mm (10 mil) to about 0.36 mm (14 mil). Most preferably, the heating element has a thickness of about 0.30 mm (12 mil). In a preferred embodiment of the invention the adhesive layer and the resistor are each 0.025 mm (1 mil) thick. Preferably, the outer layer is about 0.11 mm (4.2 mil) in thickness.

When using an acrylic adhesive, the heating element of the invention can be prepared by first carefully cleaning the resistor and one side of the sheet of metal using techniques well known in the art. A sheet of adhesive is placed on top of the cleaned surface of the sheet of metal and the resistor material is then placed on top of the adhesive layer. The resulting composite is laminated by placing it in a press and subjecting it to a temperature of about 188° C. (370° F.) and a pressure of about 827 kPa (120 psi) for about 45 minutes and then cooling for about 20 minutes under the same pressure. The laminate is then resist coated using methods well known in the art, exposed, developed, etched, stripped, dried and punched in the usual way to provide the etched resistor 12. The sheet of metal is folded and the resulting folded unit is laminated by placing it in a press at about 188° C. (370° F.) and about 117 kPa (17 psi) of pressure for about 45 minutes. The resulting element is cooled for about 20 minutes under the same pressure to give the heating element of the invention.

The heating element of the invention serves as the cutting means is the sterile docking apparatus described and claimed in U.S. patent application Ser. No. 267,291, now U.S. Pat. No. 4,369,779.

FIG. 3 shows a sterile connection apparatus according to U.S. Pat. No. 4,369,779. In operating the device, the operator inserts the ends of the tubes in slots 21-22 and 23-24 of mounting blocks 34 and 35. Heating element 10 can be mounted to block 37, which in this embodiment serves as a holder rather than a heater, and activated by conventional means. Heating element 10 and block 37 are lowered so that heating element 10 is positioned between stopblock 28 and mounting blocks 34 and 35 in alignment with the space between said mounting blocks. This positioning is effected by having the mounting blocks and block 37 fixedly arranged in a suitable housing (not shown).

The heating element is activated. The operator pushes handle 29 which moves blocks 17 and 18 together on slides 25, 26 and 27, thereby moving the tubes across heating element 10. Block 34 strikes stopblock 28 first thereby causing the two blocks to become sufficiently disengaged (as described in U.S. Pat. No. 4,369,779) so that block 35 moves on to stop against stopblock 28. This further movement by block 35 aligns slots 21 and 24 as the cut tube ends remain sealed by molten polymer against heating element 10. The operator immediately withdraws handle 29 to move block 35 which is connected to handle 29 and, by friction between the blocks through pressure exerted by a pin (not shown) on block 35, block 34 also. The blocks and the tube ends to be joined move back away from heating element 10. As the corner of block 35 leaves the edge of block 28, a spring (not shown) urges part 31 of block 35 to rotate slightly about bolt 33 toward block 34 so that slight compression is urged on the tube ends being joined as they slide off the edge of the heating element. Stop 38 on slide 25 completes the motion of the blocks and handle. When used as such, the heating element gives improved results. The absence of a polyimide insulating layer permits more uniform and rapid transfer of heat. It has been found that with an insulator present the resistor frequently had to be heated to temperatures of about 427° C. (800° F.) in order for the surface of the cutting means to be at a temperature of about 260° C. (500° F.), which is the preferred operating temperature of the apparatus. Internal temperatures of about 427° C. exceed the stability range of the polyimide insulation. With the heating element of the present invention a significantly lower gradient and quicker response between surface temperature and temperature of the resistor are obtained. Moreover, the sheet of folded metal which serves as the outer surface of the blade provides the necessary mechanical strength, assures good thermal conduction from one side of the cutting means to the other, and provides a seal between the laminating adhesive, which may soften at the temperatures encountered, and the tubes. In the latter respect, the heating element of the present invention, as compared to a prior art cutting means, eliminates a potential source for causing weakness in the tube joint and contamination of the insides of the tubes. When using the heating element of the invention as the cutting means in the aforesaid sterile docking apparatus a temperature of about 271° C. (520° F.) is preferably utilized.

Although the present invention has been described with respect to a specific embodiment, it is not limited thereto but is of the full scope of the appended claims.

We claim:

1. A heating element for sterilely welding first and second thermoplastic tubes together transversely of the axis of each tube consisting essentially of as an outer layer, a folded sheet of metal having a thermal conductivity of at least about 173 watts/m °K. at a 0.10 mm thickness and a tensile yield strength of at least about $34 \times 10^4$ kPa at a 0.10 mm thickness, a resistor disposed inside the fold of said folded sheet of metal; a layer of dielectric adhesive, stable to about 260° C., between inner surfaces of said folded sheet of metal and surfaces of said resistor, thereby electrically insulating the resistor from the folded sheet and bonding the resulting structure together; said resistor having exposed terminals for reception of electrical current and the folded edge of said metal sheet being the melting edge of the heating element.

2. A heating element according to claim 1 wherein the resistor has a positive thermal coefficient of resistance and said heating element has a thickness of from about 0.13 mm to about 0.76 mm.

3. A heating element according to claim 2 wherein the metal of the folded sheet is selected from the group consisting of copper, aluminum, silver, gold and alloys of any of the foregoing.

4. A heating element according to claim 3 wherein the resistor is an etched foil resistor.

5. A heating element according to claim 4 wherein the etched foil resistor is made of stainless steel or of Nichrome having 15% chromium by weight.

6. A heating element according to claim 5 wherein the adhesive is an epoxy or an acrylic adhesive.

7. A heating element according to claim 6 wherein the adhesive is an acrylic adhesive.

8. A heating element according to claim 7 wherein the outer layer is made of copper.

9. A heating element according to claim 8 wherein the etched foil resistor is made of stainless steel.

10. In an apparatus for forming a sterile connection between two thermoplastic tubes which comprises a heatable cutting means, a pair of mounting blocks adapted to receive and hold the two tubes, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and said cutting means while urging said blocks together; the improvement comprising that the cutting means is a heating element consisting essentially of, as an outer layer, a folded sheet of a metal having a thermal conductivity of at least about 173 watts/m °K. at a 0.10mm thickness and a tensile yield strength of at least about $34 \times 10^4$ kPa at a 0.10 mm thickness, a resistor disposed inside the fold of said folded sheet of metal; and a layer of dielectric adhesive, stable to about 260° C., between inner surfaces of said folded sheet of metal and surfaces of said resistor, thereby electrically insulating the resistor from the folded sheet and bonding the resulting structure together; said resistor having exposed terminals for reception of an electrical current and the folded edge of said metal sheet being the melting edge of the heating element.

11. An apparatus according to claim 10 wherein the resistor has a positive thermal coefficient of resistance.

12. An apparatus according to claim 11 wherein the metal is selected from the group consisting of copper, aluminum, silver, gold and alloys of any of the foregoing.

13. An apparatus according to claim 12 wherein the resistor is an etched foil resistor.

14. An apparatus according to claim 13 wherein the etched foil resistor is made of stainless steel or of Nichrome having 15% chromium by weight.

15. An apparatus according to claim 14 wherein the adhesive is an epoxy or acrylic adhesive.

16. An apparatus according to claim 15 wherein the adhesive is an acrylic adhesive.

17. An apparatus according to claim 16 wherein the outer layer is made of copper.

18. An apparatus according to claim 17 wherein the etched foil resistor is made of stainless steel.

19. An apparatus according to claim 18 wherein the heating element has a thickness of from about 0.13 mm to about 0.76 mm.

20. An apparatus according to claim 19 wherein the heating element has a thickness of from about 0.25 mm to about 0.36 mm.

21. An apparatus according to claim 20 wherein the heating element has a thickness of about 0.30 mm.

22. An apparatus according to claim 10 or 21 wherein the folded metal sheet has two openings on one of its folded sides, thereby exposing said terminals of the resistor.

* * * * *